(12) United States Patent
Tuck et al.

(10) Patent No.: US 6,204,395 B1
(45) Date of Patent: Mar. 20, 2001

(54) PROCESS FOR THE PREPARATION OF BUTANE-1,4-DIOL, γ-BUTYROLACTONE AND TETRAHYDROFURAN

(75) Inventors: Michael W. M. Tuck, London; Michael A. Wood, Yarm; Andrew G. Hiles, Buckinghamshire, all of (GB)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/554,239

(22) PCT Filed: Nov. 2, 1998

(86) PCT No.: PCT/GB98/03257

§ 371 Date: Jun. 29, 2000

§ 102(e) Date: Jun. 29, 2000

(87) PCT Pub. No.: WO99/25675

PCT Pub. Date: May 27, 1999

(30) Foreign Application Priority Data

Nov. 14, 1997 (GB) .................................................. 9724195

(51) Int. Cl.[7] ...................... C07D 307/08; C07D 307/58; C07C 29/149
(52) U.S. Cl. ........................... 549/325; 568/864; 549/508
(58) Field of Search .................................. 549/325, 508; 568/864

(56) References Cited

U.S. PATENT DOCUMENTS

| | | | |
|---|---|---|---|
| 2,638,481 | 5/1953 | Nachod, Jr. | 260/533 |
| 2,893,924 | 7/1959 | Courtier | 202/42 |
| 3,040,059 | 6/1962 | Hoyte | 260/346.4 |
| 3,818,680 | 6/1974 | Marquis | 55/48 |
| 3,850,758 | 11/1974 | Smith et al. | 203/38 |
| 3,891,680 | 6/1975 | Katsumoto et al. | 260/346.8 M |
| 4,071,540 | 1/1978 | Marquis | 260/346.76 |
| 4,118,403 | 10/1978 | White | 260/346.76 |
| 4,584,419 | 4/1986 | Sharif et al. | 568/864 |
| 4,767,869 | 8/1988 | Harrison et al. | 549/295 |
| 4,919,765 | 4/1990 | Wilkes et al. | 203/64 |
| 4,945,173 | 7/1990 | Wood | 549/295 |
| 5,254,758 | 10/1993 | Hiles et al. | 568/881 |
| 5,310,954 | 5/1994 | Hiles et al. | 549/429 |
| 5,347,021 | 9/1994 | Taylor et al. | 549/325 |

FOREIGN PATENT DOCUMENTS

| | | | |
|---|---|---|---|
| 0 373 947 B1 | 9/1993 | (EP) | 31/20 |
| 1125014 | 4/1955 | (FR) . | |
| 2 285 386 | 4/1976 | (FR) | 307/60 |
| 727828 | 4/1955 | (GB) | 1/1 |
| 763339 | 12/1956 | (GB) | 1/1 |
| 768551 | 2/1957 | (GB) | 2/3 |
| WO 86/03189 | 6/1986 | (WO) | 29/17 |
| WO 88/00937 | 2/1988 | (WO) | 29/136 |
| WO 91/01960 | 2/1991 | (WO) | 29/14 |
| WO 96 29323 * | 9/1996 | (WO) . | |
| WO 96/29323 | 9/1996 | (WO) | 307/60 |
| WO 97 43234 * | 11/1997 | (WO) . | |
| WO 97/43234 | 11/1997 | (WO) | 29/149 |
| WO 98 37051 * | 8/1998 | (WO) . | |
| WO 98/37051 | 8/1998 | (WO) | 51/573 |

OTHER PUBLICATIONS

Vapour Phase Hydrogenation of Maleic Anhydride to γ–Butyrolactone; 3. Reaction Pathway and New ctalyst Compositions, pp. 174–178; BD. 48, Heft 4/5, Apr./May 1995.

* cited by examiner

*Primary Examiner*—Bernard Dentz
(74) *Attorney, Agent, or Firm*—Nixon & Vanderhye P.C.

(57) ABSTRACT

A process is described for the production of butane-1,4-diol, γ-butyrolactone and/or tetrahydrofuran. A vaporous stream containing maleic anhydride, water, and carbon oxides is contact in an absorption zone with a high boiling ester as solvent to form a solution of maleic anhydride in the high boiling ester which has a boiling point at the atmospheric pressure at least about 30° C. higher than that of maleic anhydride and is selected from di-($C_1$ to $C_4$ alkyl) esters of alkyl dicarboxylic acids containing up to 3 carbon atoms, mono- and di-($C_{10}$ to $C_{18}$ alkyl) esters of maleic acid, fumaric acid, succinic acid, and mixtures thereof, ($C_1$ to $C_4$ alkyl) esters of naphthalene-monocarboxylic acids, tri-($C_1$ to $C_4$ alkyl) esters of aromatic tricarboxylic acids, and di-($C_1$ to $C_4$ alkyl) esters of isophthalic acid. The maleic anhydride in the solution is stripped with a gaseous stream containing hydrogen thereby forming a vaporous stream comprising hydrogen and maleic anhydride, which is contacted in a hydrogenation zone with a heterogeneous hydrogenation catalyst to convert maleic anhydride to at least one $C_4$ compound selected from butane-1,4-diol, γ-butyrolactone and tetrahydrofuran.

15 Claims, 1 Drawing Sheet

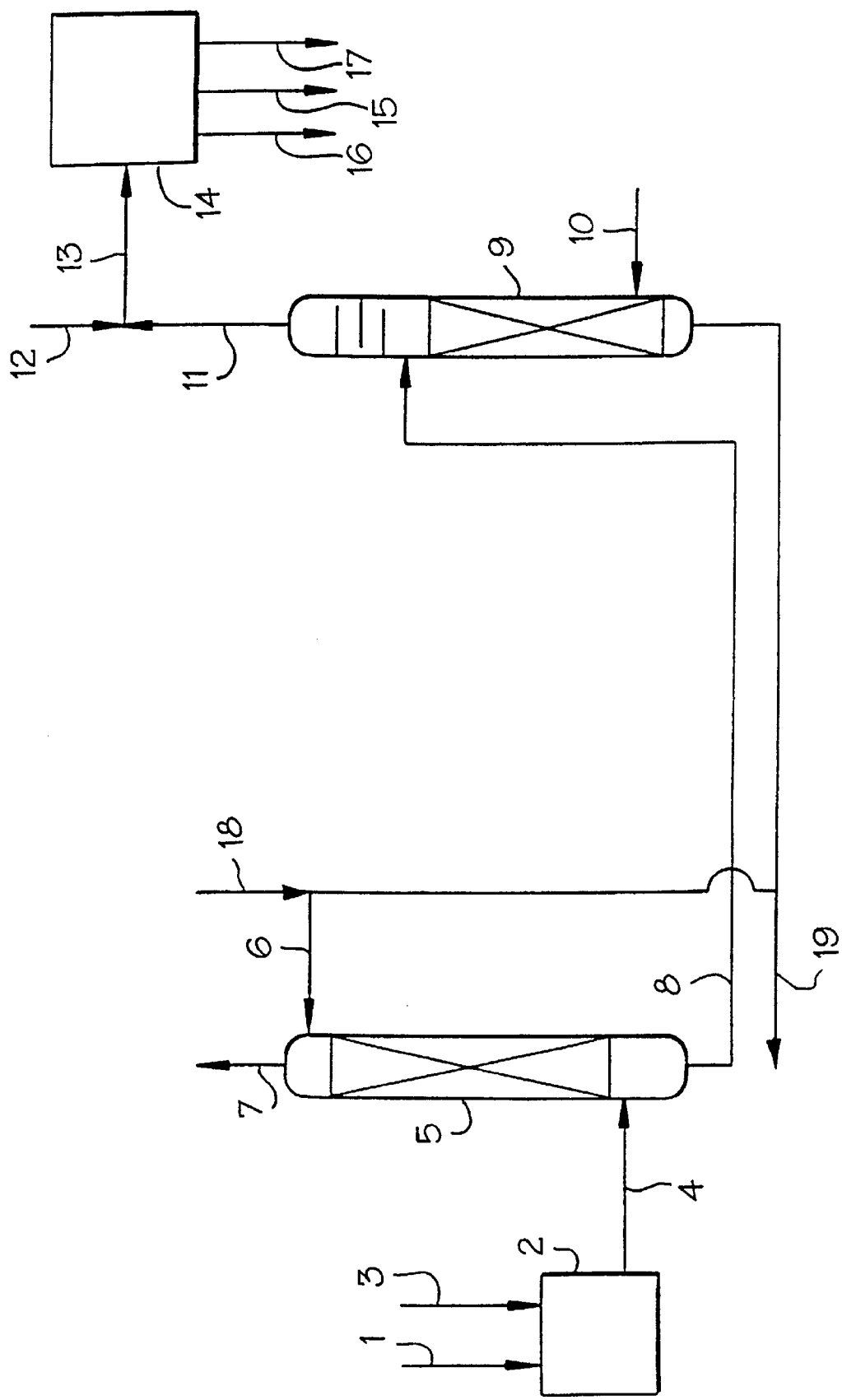

US 6,204,395 B1

PROCESS FOR THE PREPARATION OF BUTANE-1,4-DIOL, γ-BUTYROLACTONE AND TETRAHYDROFURAN

This application is a 371 of PCT/GB/03257 filed Nov. 2,1998.

This invention relates to the production of butane-1,4-diol, γ-butyrolactone and tetrahydrofuran.

Butane-1,4-diol, together with variable amounts of γ-butyrolactone and tetrahydrofuran, can be produced by hydrogenolysis of maleic anhydride. A major use of butane-1,4-diol is as a feedstock for the plastics industry, particularly for the production of polybutylene terephthalate. It is also used as an intermediate for the production of γ-butyrolactone and of the important solvent, tetrahydrofuran.

Maleic anhydride is normally produced by vapour phase oxidation of a hydrocarbon feedstock, such as benzene, mixed $C_4$ olefins, or n-butane, in the presence of a partial oxidation catalyst. In the partial oxidation of benzene there is typically used a supported vanadium pentoxide catalyst promoted with $MoO_3$ and possible other promoters. The reaction temperature is form about 400° C. to about 455° C. and the reaction pressure is form about 1 bar to about 3 bar, while about 4 times the theoretical amount of air is used in order to stay outside the explosive limits. The contact time is about 0.1 s. When the feedstock is a mixed $C_4$ olefin feedstock, i.e. a mixed butanes feedstock, then the partial oxidation catalyst may be vanadium pentoxide supported on alumina. Typical reaction conditions include use of a temperature of from about 425° C. to about 485° C. and a pressure of from about 1.70 bar to about 2.05 bar. The volume ratio of air to butanes may be about 75:1 in order to stay below explosive limits. Alternatively it is possible, according to more modern practice, to design the plant so that satisfactory safe operation can be achieved, despite the fact that the feed mixture of air and butanes is with in the flammable limits. In the case of n-butane as feedstock, the catalyst is typically vanadium pentoxide and the reaction conditions include use of a temperature of from about 350° C. to about 450° C. and a pressure fo from about 1 bar to about 3 bar. The air: n-butane volume ratio may be about 20:1, even though this may be within the flammable limits. One design of reactor for such partial oxidation reactions comprises vertical tubes surrounded by a jacket through which a molten salt is circulated in order to control the reaction temperature.

In each case a hot vaporous reaction mixture is recovered from the exit end of the reactor which comprises maleic anhydride vapour, water vapour, carbon oxides, oxygen, nitrogen, and other inert gases, besides organic impurities such as formic acid, acetic acid, acrylic acid, and unconverted hydrocarbon feedstock.

One way of recovering maleic anhydride from such a reaction mixture is to cool it to about 150° C. using a stream-producing stream and then to cool it further to about 60° C. by cooling it against water in order to condense part of the maleic anhydride, typically about 30% to about 60% of the maleic anhydride present. The remainder of the stream is then scrubbed with water.

Scrubbing with water or with an aqueous solution or slurry is described, for example in U.S. Pat. No. 2,638,481. Such scrubbing results in production of a solution of maleic acid which is then dehydrated, by distilling with xylene, for example, so as to remove the water and re-form the anhydride. A disadvantage of such a procedure, however, is that an unacceptable proportion of the product remains in the vapour phase. In addition, some of the maleic acid is inevitably isomerised to fumaric acid. The byproduct fumaric acid represents a loss of valuable maleic anhydride and is difficult to recover from the process system since it tends to form crystalline masses which give rise to process problems.

Because of this isomerisation problem a variety of other anhydrous scrubbing liquids have been proposed. For example, dibutyl phthalate has been proposed as scrubbing liquid in GB-A-727828, GB-A-763339, and GB-A-768551. Use of dibutyl phthalate containing up to 10 weight % phthalic anhydride is suggested in U.S. Pat. No. 4,118,403. U.S. Pat. No. 3,818,680 teaches use of a normally liquid intramolecular carboxylic acid anhydride, such as a branched chain $C_{12-15}$-alkenyl substituted succinic anhydride, for absorption of maleic anhydride from the reaction mixture exiting the partial oxidation reactor. Tricresyl phosphate has been proposed for this purpose in FR-A-1125014. Dimethyl terephthalate is suggested for this duty in JP-A-32-8408 and dibutyl maleate in JP-A-35-7460. A high molecular weight was as scrubbing solvent is taught in U.S. Pat. No. 3,040,059, while U.S. Pat. No. 2,893,924 proposes scrubbing with diphenylpentachloride. Use of an aromatic hydrocarbon solvent having a molecular weight between 150 and 400 and a boiling point above 140° C. at a temperature above the dew point of water in the vaporous reaction mixture, for example dibenzylbenzene, is suggested in FA-A-2285386. Absorption of maleic anhydride from the vaporous partial oxidation reaction mixture in dimethylbenzophenone followed by distillation in described in U.S. Pat. No. 3,850,758. Polymethylbenzophenones, at least a portion of which contain at least 3 methyl groups, can be used as liquid absorbent for maleic anhydride according to U.S. Pat. No. 4,071,540. Dialkyl phthalate esters having $C_4$ to $C_8$ alkyl groups and a total of 10 to 14 carbon atoms in both alkyl groups are proposed for absorption of maleic anhydride from the reaction mixture in U.S. Pat. No. 3,891,680. An ester of a cycloaliphatic acid, for example dibutyl hexahydrophthalate, is suggested as absorption solvent for maleic anhydride in ZA-A-80/1247.

It has also been proposed to effect direct condensation of maleic anhydride from the reaction mixture exiting the partial oxidation reactor. However, this procedure is inefficient because an unacceptable proportion of the maleic anhydride remains in the vapour phase.

The maleic anhydride product recovered following condensation or by scrubbing or absorption and distillation can then be subjected to hydrogenation to yield butane-1,4-diol, together with variable amounts of γ-butyrolactone and tetrahydrofuran, as described in U.S. Pat. No. 5,347,021 and EP-B-0373947 the disclosure of which is herein incorporated by reference.

It would be desirable to improve the production of butane-1,4-diol, γ-butyrolactone and tetahydrofuran, from maleic anhydride by hydrogenation. In particular it would be desirable to reduce the capital cost of construction of such a plant and also to reduce its running costs, thereby making butane-1,4-diol, γ-butyrolactone and tetrahydrofuran more readily available.

It is accordingly an object of the present invention to improve the production of butane-1,4-diol, γ-butyrolactone and tetrahydrofuran from maleic anhydride.

According to the present invention there is provided a process for the production of at least one $C_4$ compound selected from butane-1,4-diol, γ-butyrolactone and tetrahydrofuran, which includes the step of hydrogenation in the vapour phase of maleic anhydride in the presence of a heterogeneous hydrogenation catalyst, which process comprises:

(a) contacting a vaporous stream containing maleic anhydride vapour, water vapour, and carbon oxides in an absorption zone with a high boiling ester as solvent thereby to form a solution of maleic anhydride in the high boiling ester, said high boiling ester having a boiling point at atmospheric pressure which is at least about 30° C. higher than that of maleic anhydride and being selected from di-($C_1$ to $C_4$ alkyl) esters of alkyl dicarboxylic acids containing up to 13 carbon atoms, mono- and id-($C_{10}$ to $C_{18}$ alkyl) esters of maleic acid, fumaric acid, succinic acid, and mixtures thereof, ($C_1$ to $C_4$ alkyl) esters of maphthalenemonocarboxylic acids, tri-($C_1$ to $C_4$ alkyl) esters of aromatic tricarboxylic acids, and di-($C_1$ to $C_4$ alkyl) esters of isophthalic acid;

(b) recovering form the absorption zone a waste gas stream;

(c) contacting the solution of maleic anhydride in the high boiling ester with a gaseous stream containing hydrogen thereby to strop maleic anhydride therefrom and to form a vaporous stream comprising hydrogen and maleic anhydride;

(d) contacting material of the vaporous stream of step (c) in a hydrogenation zone under hydrogenation conditions with a heterogeneous hydrogenation catalyst thereby to convert maleic anhydride by hydrogenation to at least one $C_4$ compound selected from butane-1,4-diol, γ-butyrolactone and tetrahydrofuran; and (e) recovering from the hydrogenation zone a product stream containing said at least one $C_4$ compound.

The vaporous stream of step (a) of the process of the invention is preferably produced by partial oxidation of a hydrocarbon feedstock in the presence of a partial oxidation catalyst using molecular oxygen, typically in the form of air. The hydrocarbon feedstock can be benzene, or a mixed $C_4$ olefin stream, but is most preferably n-butane. The use of n-butane as hydrocarbon feedstock is currently preferred upon the grounds of cost since it is a cheaper feedstock than benzene or butenes. Hence in the process of the invention the feedstock used for production of the maleic anhydride containing vaporous stream of step (a) is most preferably n-butane and the catalyst is preferably vanadium pentoxide. Typical partial oxidation conditions in this case include use of a temperature of from about 350° C. to about 450° C. and a pressure of from about 1 bar to about 3 bar, an air to n-butane ratio of from about 15:1 to about 50:1, e.g. about 20:1 and a partial oxidation catalyst comprising vanadium pentoxide; the contact time is typically from about 0.01 s to about 0.5 s, e.g. about 0.1 s.

Partial oxidation of the hydrocarbon feedstock is conveniently conducted in a reactor which comprises vertical tubes surrounded by a jacket through which a molten salt is circulated in order to control the reaction temperature. The vaporous stream from the partial oxidation reactor can then be cooled by external cooling with boiler feed water to raise steam, and possibly also by further external cooling with cooling water to a temperature in the range of from about 60° C. to about 160° C.

In step (a) of the process of the invention the vaporous maleic anhydride stream is preferably contacted with the high boiling ester at a temperature in the range of from about 60° C. to about 160° C., preferably from about 80° C. to about 120° C., and at a pressure of from about 1 bar to about 3 bar so as to form a solution comprising maleic anhydride in the high boiling ester. The contacting can be carried out by bubbling the vaporous stream through a body of the high boiling ester. Alternatively the high boiling ester can be sprayed into the vaporous stream. Countercurrent contacting devices can also be employed wherein the ascending vaporous stream is contacted by a descending stream of high boiling ester in a gas-liquid contacting device, such as a packed scrubber tower or a scrubber tower provided with trays. In this step the high boiling ester will typically be at a lower temperature than the vaporous stream so that the latter is cooled.

In the resulting solution of maleic anhydride in the high boiling ester the concentration of maleic anhydride in the high boiling ester may range from about 100 g/l to about 400 g/l.

The high boiling ester has a boiling point at atmospheric pressure that is at least about 30° C. higher, and preferably at least about 60° C. to about 70° C. higher, than that of maleic anhydride. As examples of esters of alkyl dicarboxylic acids containing up to 13 carbon atoms from which a suitable high boiling ester can be selected there can be mentioned dimethyl, diethyl, di-n- or -iso-propyl, di-n-sec-, or iso-butyl esters of suberic acid, azelaic acid, sebacic acid, undecanedioic acid, dodecanedioic acid, and tridecanedioic acid, It is preferred that the alkyl moiety in such an ester shall be derived from the same alkanol as the $C_1$ to $C_4$ alkanol used in the esterification step (c). In this way any transesterification reactions that may occur do not give rise to additional ester. Thus when the alkanol used is methanol and the dialkyl maleate is dimethyl maleate, any ester used as the high boiling ester is preferably also a dimethyl ester, such as dimethyl sebacate.

The high boiling ester may alternatively be selected from mono- and di-($C_{10}$ to $C_{18}$ alkyl) esters of one of the $C_4$ alkyl dicarboxylic acids, i.e. maleic acid, fumaric acid, and succinic acid, and mixtures thereof. Examples of such esters include the esters and mixtures thereof derived form n-decyl alcohol, lauryl alcohol, myristyl alcohol, cetyl alcohol, stearyl alcohol, and eicosanol.

The high boiling ester may alternatively be selected form ($C_1$ to $C_4$ alkyl) esters of maphthalenemonocarboxylic acids, such as methyl naphthalene-2-carboxylate, from tri-($C_1$ to $C_4$ alkyl) esters of aromatic tricarboxylic acids, such as trimethyl benzene-1,2,4-tricarboxylate, or from di-($C_1$ to $C_4$ alkyl) esters of isophthalic acid, such as dimethyl isophthalate.

The high boiling ester used in step (a) conveniently comprises material resulting from the hydrogen stripping step (c).

Provided that appropriate conditions are adopted in step (a), the gas stream recovered in step (b) of the process of the invention can be essentially free from maleic anhydride.

In step (c) of the process of the invention, a gas stream comprising hydrogen is passed through the solution of maleic anhydride.

The hydrogen stripping step is preferably conducted substantially at or at a pressure slightly higher than the inlet pressure to the hydrogenation zone. The hydrogen stripping step is similarly preferably conducted at substantially the desired inlet temperature to the hydrogenation zone or a little below this temperature, for example from about 5° C. to about 20°C. below this temperature. Then the temperature can be raised to the desired inlet temperature by admixture of further hot hydrogen-containing gas which has the additional benefit of diluting the vaporous ester-containing stream and thereby ensuring that it is at a temperature above its dew point, preferably at least about 5° C. higher than its dew point.

The hydrogenation step is advantageously conducted in the vapour phase, using a heterogeneous hydrogenation catalyst. Typical hydrogenation catalysts include promoted copper-based catalysts, such as a Cu/Zn/Mg/Cr catalyst of the type described in J. Org. Chem 150, pages 177 to 185.

The catalyst particles preferably have a particle size in the range of from about 0.5 mm to about 5 mm. The particles may be of any convenient shape, e.g. spheres, pellets rings or saddles. When using a fixed bed of catalyst the reactor can be a shell-and-tube reactor, which can be operated substantially isothermally; however, it is preferably an adiabatic reactor. The use of an adiabatic reactor is advantageous since its capital cost is much lower than that of a shell-and-tube reactor and it is generally much easier to charge the reactor with the chosen catalyst.

Hydrogenation is conducted at an elevated temperature of, for example, from about 150° C. to about 300° C., more usually from about 180° C. to about 280° C., and at a pressure of from about 5 bar to about 100 bar, preferably from about 10 bar to about 70 bar.

From the hydrogenation zone there is recovered a hydrogenation product mixture which contains, in addition to butane-1,4-dio, also some tetrahydrofuran and γ-butyrolactone. Even if the primary product of interest is butane-1,4-diol, the presence of tetrahydrofuran and γ-butyrolactone is not disadvantageous since these compounds are important chemicals of commerce and it is accordingly economic to recover them in pure form. If desired, γ-butyrolactone can be recycled to the hydrogenation zone to produce additional butane-1,4diol.

For further details regarding vapour phase hydrogenation of maleic anhydride reference may be made to a paper by G. L. Castiglioni et al in Erdöl und Kohle - Erdgas - Petrochemie vereinigt mit Brennstoff-Chemie, Bd. 48, Heft 4/5, April/May 1995 at pates 174 to 178 under the heading Wissenschaft & Technik (Science & Technology). Subsequent purification of the resultant crude hydrogenation product mixture can be carried out in a manner analogous to that described in U.S. Pat. No. 4,584,419, WO-A-86/03189, WO-A-88/0937, U.S. Pat. No. 4,767,869, U.S. Pat. No. 4,945,173, U.S. Pat. No. 4,919,765, U.S. Pat. No. 5,254,758, U.S. Pat. No. 5,310,954, and WO-A- 91/01960.

In order that the invention may be clearly understood and readily carried into effect a plant for the production of butane-1,4,-diol, as well as some γ-butyrolactone and tetrahydrofuran, using a preferred process in accordance with the present invention will now be described, by way of example only, with reference to the accompanying drawing which is a flow diagram of the plant.

Referring to the drawing, n-butane is supplied in line 1 at a pressure of from 1 to 3 bar and at a temperature of 400° C. to a partial oxidation plant 2 which is also supplied with air in line 3. Partial oxidation plant 2 is of conventional design and includes a partial oxidation reactor comprising tubes packed with a partial oxidation catalyst consisting of vanadium pentoxide packed into tubes provided with a jacket through which molten salt can be circulated for the purpose of temperature control. The partial oxidation reactor is operated at an air: n-butane feed ration of 20:1.

A hot vaporous partial oxidation product stream is cooled by external cooling against boiler feed water to raise steam and then against cooling water to reduce its temperature to 138° C. It is recovered from plant 2 in line 4. This contains 2.9% w/w maleic anhydride, 5.8% w/w water, 1.3% w/w carbon dioxide, 1.0% w/w carbon monoxide, 0.01% w/w acetic acid, 0.01% w/w acrylic acid, 15.7% w/w oxygen, and the balance essentially comprising nitrogen and other inert gases. It is fed to the bottom of a scrubbing tower 5, up which it passes against a downflowing spray of dimethyl sebacate which is supplied at a temperature of about 68° C. from line 6. The scrubbed waste gas stream which contains 0.03% w/w maleic anhydride exits the top fo scrubbing tower 5 in vent gas line 7 and is passed to a waste gas burner.

From the bottom of scrubbing tower 5 there is recovered a liquid stream in line 8 which comprises a solution of approximately 15% w/w maleic anhydride, 0.1% acetic acid, and 0.04% w/w acrylic acid in dimethyl sebacate. This is supplied to near the top of a stripping column 9 which is operated at a temperature of 180° C. and a pressure of 580 psia (40 bar). Column 9 has a number of distillation trays above the point of injection of the maleic anhydride solution into column 9 so as to reduce carryover of dimethyl sebacate in the overhead stream from column 9. The solution of maleic anhydride in dimethyl sebacate flows down stripping column 9 against an upflowing stream of hydrogen from line 10. The stripped dimethyl sebacate is recycled from the bottom of stripping column 9 by way of line 6 to the top of scrubbing tower 5. Form the top of stripping column 9 there emerges in line 11 a near saturated vapour mixture stream comprising maleic anhydride in hydrogen, with a hydrogen-:maleic anhydride molar ration of about 400:1. This vapour mixture stream is at a temperature of from about 180° C. to about 200° C. and at a pressure of about 40 bar. It is diluted with further hot hydrogen from line 12 at a temperature of from about 180° C. to about 220° C. to yield a vaporous stream with a hydrogen: maleic anhydride molar ratio of about 450:1 and is at least about 5° C. above its dew point.

This vaporous mixture passes onwards in line 13 to hydrogenation plant 14 which includes an adiabatic reactor packed with a copper based catalyst (e.g. a promoted copper catalyst) and operated at an inlet temperature of 180° C., an inlet pressure of 565 psia (39 bar), and an exit temperature of 200° C. The maleic anhydride feed rate corresponds to a liquid hourly space velocity of 0.1 $h^{-1}$. The plant also includes a purification section in which the crude hydrogenation product mixture is distilled in several stages to yield pure butane-1,4-diol in line 15. Lines for separate recovery of γ-butyrolactone and tetrahydrofuran are indicated at 16 and 17 respectively. Fresh dimethyl sebacate solvent can be added by means of line 18 while a purge stream of the recycled solvent stream can be taken in line 19.

The dimethyl sebacate used as solvent can be replaced by, for example, methyl naphthalene-2-carboxylate, trimethyl benzene-1,2,4-tricarboxylate or dimethyl isophthalate. Alternatively the dimethyl sebacate can be replaced as high boiling ester by a di-($C_{10}$ to $C_{18}$ alkyl) maleate, fumarate, or succinate or a mixture of two or more thereof, optionally in admixture with the corresponding mono-($C_{10}$ to $C_{18}$ alkyl) maleate, fumarate, or succinate or a mixture of two or more thereof, and/or with the corresponding free acid or mixture of acids, i.e. maleic acid, fumaric acid, and/or succinic acid. Typically the high boiling ester in such a case comprises predominantly the diester or diester mixture, with no more than a minor amount, typically less than about 5molar % each, of the corresponding monoester or monoester mixture and/or of the corresponding acid or mixture of acids. As an example of such a high boiling ester there can be mentioned dilauryl maleate which may contain up to about 10 molar % of dilauryl succinate as well as minor amounts, preferably less than about 5 molar % each, more preferably less than about 1 molar % each, of one or more of dilauryl fumarate, monolauryl maleate, monolauryl fumarate, and monolauryl succinate, In addition, the recycle stream in line 6 can contain a minor amount, typically less than about 10 molar % each, of maleic anhydride, maleic acid, fumaric acid, and/or succinic acid.

What is claimed is:

1. A process for the production of at least one $C_4$ compound selected from butane-1,4diol, γ-butyrolactone and tetrahydrofuran, which includes the step of hydrogenation in the vapour phase of maleic anhydride in the presence of a heterogeneous hydrogenation catalyst, which process comprises:

(a) contacting a vaporous stream containing maleic anhydride vapour, water vapour, and carbon oxides in an absorption zone with a high boiling ester as solvent thereby to form a solution of maleic anhydride in the high boiling organic solvent, said high boiling ester having a boiling point at atmospheric pressure which is at least about 30° C. higher than that of maleic anhydride and being selected from di-($C_1$ to $C_4$ alkyl) esters of alkyl dicarboxylic acids containing up to 13 carbon atoms, mono- and di-($C_{10}$ to $C_{18}$ alkyl) esters of maleic acid, fumaric acid, succinic acid, and mixtures thereof, ($C_1$ to $C_4$ alkyl) esters of maphthalenemonocarboxylic acids, tri-($C_1$ to $C_4$ alkyl) esters of aromatic tricarboxylic acids, and di-($C_1$ to $C_4$ alkyl) esters of isophthalic acid;

(b) recovering from the absorption zone a waste gas stream;

(c) contacting the solution of maleic anhydride in the high boiling ester with a gaseous stream containing hydrogen thereby to strip maleic anhydride therefrom and to form a vaporous stream comprising hydrogen and maleic anhydride;

(d) contacting material of the vaporous stream of step (c) in a hydrogenation zone under hydrogenation conditions with of a heterogeneous hydrogenation catalyst thereby to convert maleic anhydride by hydrogenation to at least one $C_4$ compound selected from butane-1,4diol, γ-butyrolactone and tetrahydrofuran; and (e) recovering from the hydrogenation zone a product stream containing said at least one $C_4$ compound.

2. A process according to claim 1, which the vaporous stream of step (a) is produced by partial oxidation of a hydrocarbon feedstock in the presence of a partial oxidation catalyst using molecular oxygen.

3. A process according to claim 2, in which the hydrocarbon feedstock is n-butane.

4. A process according to claim 3, in which the partial oxidation catalyst comprises vanadium pentoxide and in which the partial oxidation conditions include use of a temperature of from about 350° C. to about 450° C., a pressure of from about 1 bar to about 3 bar, an air to n-butane ratio of from about 15:1 to about 50:1 and a contact time of from about 0.01 s to about 0.5 s.

5. A process according to claim 1, in which in step (a) the vaporous maleic anhydride stream is contacted with the high boiling solvent at a temperature in the range of from about 60° C. to about 160° C. and at a pressure of from about 1 bar to about 3 bar so as to form a solution comprising maleic anhydride in the high boiling ester.

6. A process according to claim 5, in which the contacting step is carried out in a countercurrent contacting device wherein the ascending vaporous stream is contacted by a descending stream of high boiling ester in a gas-liquid contacting device.

7. A process according to claim 1, in which the high boiling ester is a methyl ester.

8. A process according to claim 7, in which the high boiling ester is dimethyl sebacate.

9. A process according to claim 1, in which the high boiling ester used in step (a) comprises recycled material resulting from the hydrogen stripping step (c).

10. A process according to claim 1, in which the hydrogen stripping step is conducted at substantially the inlet pressure to the hydrogenation zone.

11. A process according to claim 1, in which the hydrogen stripping step is conducted at a temperature in the range of from the inlet temperature to the hydrogenation zone to about 20° C. below the inlet temperature to the hydrogenation zone.

12. A process according to claim 1, in which the hydrogenation step is conducted in the vapour phase using a promoted copper catalyst at a temperature of from about 150° C. to about 300° C. and at a pressure of from about 5 bar to about 100 bar.

13. A process according to claim 1, in which there is recovered form the hydrogenation zone a hydrogenation product mixture which contains, in addition to butane-1,4-diol, also tetrahydrofuran and γ-butyrolactone.

14. A process according to claim 13, in which the hydrogenation product mixture is purified by distillation in one or more stages, including distillation in a "light ends" column to separate overhead the volatile components of the mixture including tetrahydrofuran, and n-butanol.

15. A process according to claim 14, in which the bottoms product from the "light ends" column is further purified by distillation in one or more stages to yield pure butane-1,4-diol.

* * * * *